(12) United States Patent
Van Stell

(10) Patent No.: US 10,578,096 B2
(45) Date of Patent: Mar. 3, 2020

(54) PERISTALTIC PUMPHEAD AND METHODS FOR ASSEMBLY THEREOF

(71) Applicant: Cole-Parmer Instrument Company LLC, Barrington, IL (US)

(72) Inventor: James Van Stell, Schaumburg, IL (US)

(73) Assignee: COLE-PARMER INSTRUMENT COMPANY LLC, Barrington, IL (US)

( * ) Notice: Subject to any disclaimer, the term of this patent is extended or adjusted under 35 U.S.C. 154(b) by 591 days.

(21) Appl. No.: 15/198,729

(22) Filed: Jun. 30, 2016

(65) Prior Publication Data

US 2018/0003169 A1 Jan. 4, 2018

(51) Int. Cl.
*F04B 43/12* (2006.01)
*F04B 49/06* (2006.01)
(Continued)

(52) U.S. Cl.
CPC .......... *F04B 43/1284* (2013.01); *F04B 43/12* (2013.01); *F04B 49/06* (2013.01);
(Continued)

(58) Field of Classification Search
CPC .. F04B 43/12; F04B 43/1223; F04B 43/1238; F04B 43/1253; F04B 43/1284;
(Continued)

(56) References Cited

U.S. PATENT DOCUMENTS 4,256,442 A * 3/1981 Lamadrid ........... F04B 43/1284
417/475
4,412,793 A 11/1983 Stenberg et al.
(Continued)

FOREIGN PATENT DOCUMENTS

| EP | 1 518 572 A1 | 3/2005 |
|---|---|---|
| EP | 1 947 340 A1 | 7/2008 |
| KR | 200463057 Y1 | 10/2012 |

OTHER PUBLICATIONS

Extended European Search Report for related foreign application No. 17176038.2 dated Nov. 9, 2017.
(Continued)

*Primary Examiner* — Patrick Hamo
*Assistant Examiner* — Chirag Jariwala
(74) *Attorney, Agent, or Firm* — Arent Fox LLP

(57) ABSTRACT

A peristaltic pump may include a rotor rotatably mounted on a base and an occlusion bed mounted on the base and moveable toward and away from the rotor. The peristaltic pump may also include a lid hingedly mounted to the base along a first hinge axis including a mounting bracket extending perpendicularly relative to the first hinge axis. A linkage assembly connecting the occlusion bed and the lid may include a pair of curved arms hingedly mounted to the mounting bracket along a second hinge axis parallel to the first hinge axis and a cam connecting the pair of curved arms and having a cam surface facing the mounting bracket, the cam being hingedly mounted to the occlusion bed at an end opposite the second hinge axis. The mounting bracket abuts the cam surface and form a cooperative connection between the lid and the occlusion bed via the linkage assembly.

13 Claims, 6 Drawing Sheets

(51) Int. Cl.
*F04B 53/16* (2006.01)
*F04B 53/22* (2006.01)
*A61M 1/10* (2006.01)

(52) U.S. Cl.
CPC .............. *F04B 53/16* (2013.01); *F04B 53/22* (2013.01); *A61M 1/1039* (2014.02)

(58) Field of Classification Search
CPC ........ F04B 49/06; F04B 49/065; F04B 53/16; F04B 53/22; F04B 9/042; F04B 9/045; A61M 1/1037; A61M 1/1039; A61M 1/1043; A61M 1/1081; A61M 2207/00; A61M 2207/10; Y10T 16/547; Y10T 16/5474; Y10T 16/5475
See application file for complete search history.

(56) References Cited

U.S. PATENT DOCUMENTS

| | | |
|---|---|---|
| 4,631,008 A | 12/1986 | Stenner |
| 5,380,173 A | 1/1995 | Hellstrom |
| 5,468,129 A | 11/1995 | Sunden et al. |
| 6,494,693 B1 | 12/2002 | Sunden |
| 7,478,999 B2 | 1/2009 | Limoges |
| D605,286 S | 12/2009 | LaBanco et al. |
| 7,874,819 B2 | 1/2011 | North |
| 7,980,835 B2 | 7/2011 | Labanco et al. |
| 8,052,399 B2 | 11/2011 | Stemple et al. |
| 9,180,241 B2 | 11/2015 | Schaefer |
| 2005/0025647 A1 | 2/2005 | Ortega et al. |
| 2005/0069436 A1 | 3/2005 | Shibasaki |
| 2008/0175734 A1 | 7/2008 | Labanco et al. |
| 2009/0129944 A1 | 5/2009 | Stemple et al. |
| 2011/0004161 A1 | 1/2011 | Ito |
| 2011/0300010 A1 | 12/2011 | Jarnagin et al. |
| 2013/0115120 A1* | 5/2013 | Jarnagin .............. F04B 43/1284 417/477.2 |
| 2015/0182688 A1* | 7/2015 | Dhami .............. A61M 5/14228 604/151 |
| 2015/0204321 A1 | 7/2015 | Schnekenburger et al. |
| 2015/0217040 A1* | 8/2015 | Matsuo ............... A61M 1/3656 417/477.1 |

OTHER PUBLICATIONS

Cole-Parmer, "Operating Manual: B/T Rapid-Load Peristaltic Pumps and Drives", Thermo Fisher Scientific Inc., 2008.

* cited by examiner

US 10,578,096 B2

PERISTALTIC PUMPHEAD AND METHODS FOR ASSEMBLY THEREOF

INTRODUCTION

The present disclosure generally relates to peristaltic pumps.

BACKGROUND

Rotary peristaltic pumps are typically used for moving liquids through flexible tubing. A typical peristaltic pump has a rotor assembly with pinch rollers that apply pressure to the flexible tubing at spaced locations to provide a squeezing action on the tubing against an occlusion bed. The occlusion of the tubing creates increased pressure ahead of the squeezed area and reduced pressure behind that area, thereby forcing a liquid through the tubing as the rotor assembly moves the pinch rollers along the tubing.

The spacing between the occlusion bed and the pinch rollers of the rotor assembly is critical for proper pump operation. The spacing between the occlusion bed and the pinch rollers is unforgiving from a tolerance standpoint since it is used both to provide a compressive force between the rotor assembly and occlusion bed and to locate the occlusion bed with respect to the rotor assembly. Tubing that is too loose in the pump may lead to flapping while tubing that is too tight may lead to excessive wear on the tubing. Improper installation of the tube may lead to poor pump performance and shortened tube life.

Various mechanisms exist in the related art for moving the occlusion bed with respect to the rotor assembly. Such mechanisms, however, often allow movement of the occlusion bed, especially when high pressures and cyclic loading are applied as the rotor assembly rotates. Further, the cyclic loading may lead to wear over prolonged use.

Accordingly, there is a need for an occlusion bed that resists movement and is durable for an operating life of the peristaltic pump.

SUMMARY

The following presents a simplified summary of one or more aspects of the invention in order to provide a basic understanding of such aspects. This summary is not an extensive overview of all contemplated aspects, and is intended to neither identify key or critical elements of all aspects nor delineate the scope of any or all aspects. Its purpose is to present some concepts of one or more aspects in a simplified form as a prelude to the more detailed description that is presented later.

In one aspect, the disclosure provides a peristaltic pump. The peristaltic pump may include a rotor rotatably mounted on a base of the peristaltic pump. The peristaltic pump may also include an occlusion bed mounted on the base of the peristaltic pump and moveable toward and away from the rotor. The peristaltic pump may also include a lid hingedly mounted to the base of the peristaltic pump along a first hinge axis, the lid having an outer surface forming a portion of the outer housing surface of the pump, and the lid including a mounting bracket extending perpendicularly relative to the first hinge axis. The lid may also include a linkage assembly connecting the occlusion bed and the lid. The linkage assembly may include a pair of curved arms hingedly mounted to the mounting bracket at a first end of each of the pair of curved arms about a second hinge axis parallel to the first hinge axis, and a cam connecting the pair of curved arms and having a cam surface facing the mounting bracket, the cam being hingedly mounted to the occlusion bed at a second end of each of the pair of curved arms, the second end of each of the curved arms being opposite to the first end. When the lid is in a first position, such as a closed position, the mounting bracket may extend between the pair of curved arms to abut the cam surface and form a cooperative connection between the lid and the occlusion bed via the linkage assembly.

In another aspect, the disclosure provides a method of assembling a peristaltic pump. The method may include: mounting a rotor on a molded base of the peristaltic pump, the base including a rotor receiving opening, a pair of elongated slots, and at least one cylindrical hinge portion; slidably mounting an occlusion bed on the base though the slots; inserting a first pivot pin along a first hinge axis through the at least one cylindrical hinge portion and corresponding cylindrical hinge portion of a lid, the lid including a mounting bracket extending perpendicularly relative to the first hinge axis; inserting a second pivot pin along a second hinge axis parallel to the first hinge axis through the mounting bracket and through a first end of each of a pair of curved arms of a linkage assembly including a cam connecting the pair of curved arms at a second end opposite the first end and having a cam surface facing the mounting bracket; and inserting a third pivot pin along a third hinge axis parallel to the first hinge axis through the cam and through a bracket of the occlusion bed. When the lid is in a closed position, the mounting bracket may extend between the pair of curved arms to abut the cam surface and form a cooperative connection between the lid and the occlusion bed via the linkage assembly.

These and other aspects of the invention will become more fully understood upon a review of the detailed description, which follows.

DETAILED DESCRIPTION

The detailed description set forth below in connection with the appended drawings is intended as a description of various configurations and is not intended to represent the only configurations in which the concepts described herein may be practiced. The detailed description includes specific details for the purpose of providing a thorough understanding of various concepts. However, it will be apparent to those skilled in the art that these concepts may be practiced without these specific details. In some instances, well known components are shown in block diagram form in order to avoid obscuring such concepts.

In an aspect, the disclosure provides for a peristaltic pump head that utilizes a centrally located linkage assembly hingedly attached between a lid and an occlusion bed. As the lid is opened, the linkage assembly pulls the occlusion bed away from the rotor and rollers to allow the tube to be replaced. As the lid is closed, the linkage assembly slides the occlusion bed toward the rotor and rollers to position the occlusion bed for pumping operation. The linkage assembly includes a cam that forms a cooperative connection between the lid and the occlusion bed, such that the occlusion bed is prevented from movement even when the tubing includes a high pressure liquid. Moreover, the linkage assembly utilizes hinged connections that distribute forces over an extended surface area to reduce wear and allow a longer useful life of the peristaltic pump head.

Figure 1:
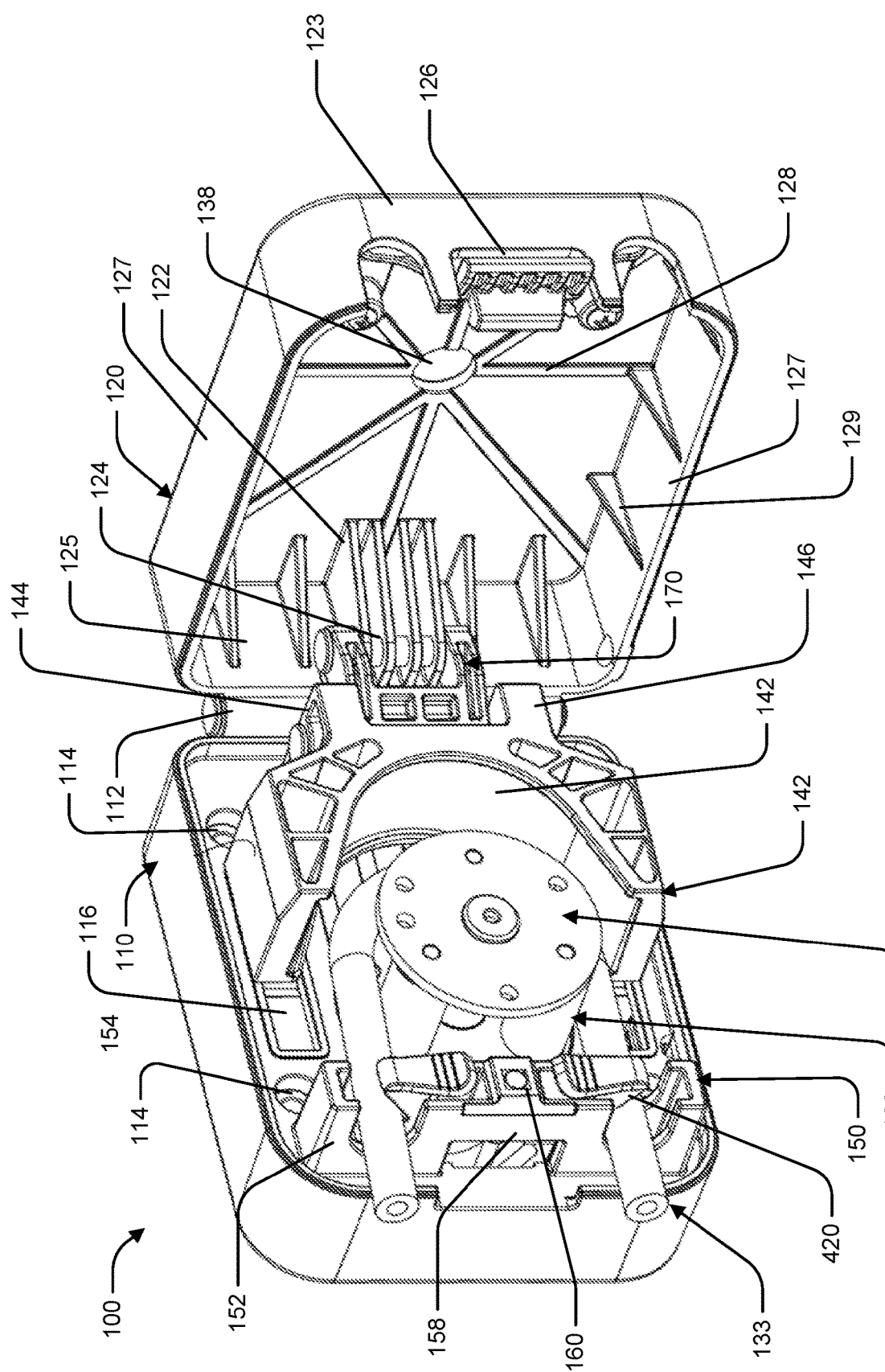
FIG. 1 is perspective view of an exemplary peristaltic pump utilizing a linkage assembly, according to an aspect of the disclosure.

FIG. 1 is perspective view of an example peristaltic pump 100 utilizing a linkage assembly 170. The peristaltic pump 100 may include a pump base 110 pivotably attached to a lid 120 via a hinge 112. The hinge 112 may include a first cylindrical hinge portion formed in the base 110 and a second cylindrical hinge portion formed in the lid 120. The pump base 110 may further include mounting holes 114 that may be used to mount the pump 100 to a housing, including a motor (not shown). The pump base 110 may also include elongated slots 116 that slidably retain an occlusion bed 140, as discussed in further detail below.

The lid 120 may include a top surface 121, a front wall 123, a rear wall 125, and side walls 127. The rear wall may include one or more cylindrical portions of the hinge 112. The lid 120 may be reinforced with supports 129 connecting the lid to the front wall, rear wall and/or side walls. The lid 120 may also include ribs 128 running along the top surface. A mounting bracket 122 may be located along the rear wall inward from the hinge 112. The mounting bracket 122 may include a cylindrical opening in the end that forms a hinge 124 with the linkage assembly 170. The hinge 124 may have an axis parallel with the axis of the hinge 112. In an aspect, the mounting bracket 122 may be or include a boss that extends from the top surface and the rear wall to an end located toward the base 110. The connection to both the top surface and rear wall may help distribute forces across the peristaltic pump 100. In an aspect, as illustrated, the boss of the mounting bracket 122 may be formed from a plurality of parallel fins, which may result in a durable mounting bracket having a low weight. The mounting bracket 122 may also be a solid boss. The lid 120 further includes a latch 126 on the front wall. For example, the latch 126 may include a flexible or pivotable tab having a ramp surface that slides over a ledge 158 of the base 110 and a shoulder that engages the ledge once the ramp surface clears the ledge.

A rotor 130 may be generally centrally located within the pump base 110. The rotor 130 may extend through the pump body and may be driven by a motor (not shown) to rotate within the pump 100 about a rotor axis. The rotor 130 may include a plurality of rollers 132. Each roller 132 may be rotatable about an axis parallel with the rotor axis. In an aspect, the rotor 130 may also include a drive feature 134 (best seen in FIG. 6D) for engaging a motor (not shown) and/or a seal (not shown) for isolating the pump 100 from the motor. In an aspect, a portion of the rotor 130 may extend through an opening 138 in the lid 120.

The base 110 may slidably mount an occlusion bed 140 in the slots 116. The occlusion bed 140 may include a curved occlusion surface 142. In operation, as the rotor 130 rotates, the rollers 132 may squeeze the tubing 136 against the occlusion surface 142 to force fluid through the tubing 136 in a peristaltic action. In an aspect, as illustrated, the occlusion bed 140 may include a rigid body supporting the occlusion surface 142. For example, the rigid body may include a solid member and/or a plurality of braces. The rigid body may transfer forces from the occlusion surface 142 to an occlusion bracket 144. The rigid body may also separate the occlusion surface 142 from the occlusion bracket 144 such that any particulates from wear on the occlusion bracket are unlikely to contact or contaminate the occlusion surface 142. The occlusion bracket 144 may be hingedly connected to the linkage assembly 170 to form a hinge 146. The occlusion bracket 144 may include a pair of bosses each having a cylindrical opening. The bosses may be spaced apart to distribute forces from the entire occlusion surface 142. For example, a distance between the bosses may be approximately half of the width of the occlusion bed 140.

The base 110 may further include a tubing retaining assembly 150 for retaining the tubing 136 that holds the operating fluid of the pump 100. The tubing retaining assembly 150 may prevent longitudinal movement of the tube as the rollers 132 provide both lateral compressive forces and longitudinal forces on the tubing 136. The tubing retaining assembly 150 may include a retainer housing 152 and a pair of pivoting retainers 154, for example. The retainers 154 may each include a grip to manually pivot the respective retainers 154 inward and away from a side wall of the retainer housing 152. The retainers 154 may also each include a tubing engaging notch 420 that contacts the emplaced tubing 136 to prevent longitudinal movement while allowing fluid to flow within the tubing 136. For example, the retainers 154 may be biased toward the side walls of the retainer housing 152 and hold the tubing 136 against the side walls to prevent longitudinal movement. In an aspect, the pivoting retainers 154 are mounted to and pivot about shafts secured within the retainer housing 152. The retainers 154 may be biased by a biasing element. For example, the retainer arms may be connected to each other at an end opposite the grip via an elastic member, such as a spring. The elastic member may provide a force to bias the tubing engaging notches of the retainers 154 outward toward the side walls of the retainer housing 152 as illustrated by arrows 510 in FIG. 5.

The retainer housing 152 may further include a sensor 160 for sensing when the lid 120 is in the closed position. The sensor 160 may include a button, proximity sensor, magnetic sensor, or other sensing device that determines whether the lid 120 is closed. When the lid 120 is closed, the sensor 160 may further include electronic and/or other components to cause engagement of the rotor 130 with the motor (not shown) and/or allow activation of the motor.

The linkage assembly 170 may connect the occlusion bed 140 to the mounting bracket 122 of the lid 120. The linkage assembly 170 may include a cam 320 (FIG. 3) connecting at least two curved arms 310 (FIG. 3). The curved arms 310 may have a concave aspect facing toward the base 110, for example. The curved arms 310 may each include an opening at the end opposite the cam 320 that retains a hinge pin to cooperatively Balm the hinge 124 with the mounting bracket 122. The cam 320 may include, for example, a cylindrically-shaped opening that retains a hinge pin to form the hinge 146 with the occlusion bracket 144. The cam 320 may be centered along an axis of rotation of the rotor 130 and extend approximately half of the width of the occlusion bed 140, for example. Accordingly, forces exerted by the rotor 130 on the occlusion bed 140 may be distributed across the cam. The cam may further include a cam surface 324 (FIG. 3) located between the curved arms. When the lid 120 is closed, the cam surface 324 may contact the mounting bracket 122 to form an abutting connection between the lid 120 and the occlusion bed 140 via the cam 320.

Figure 2:
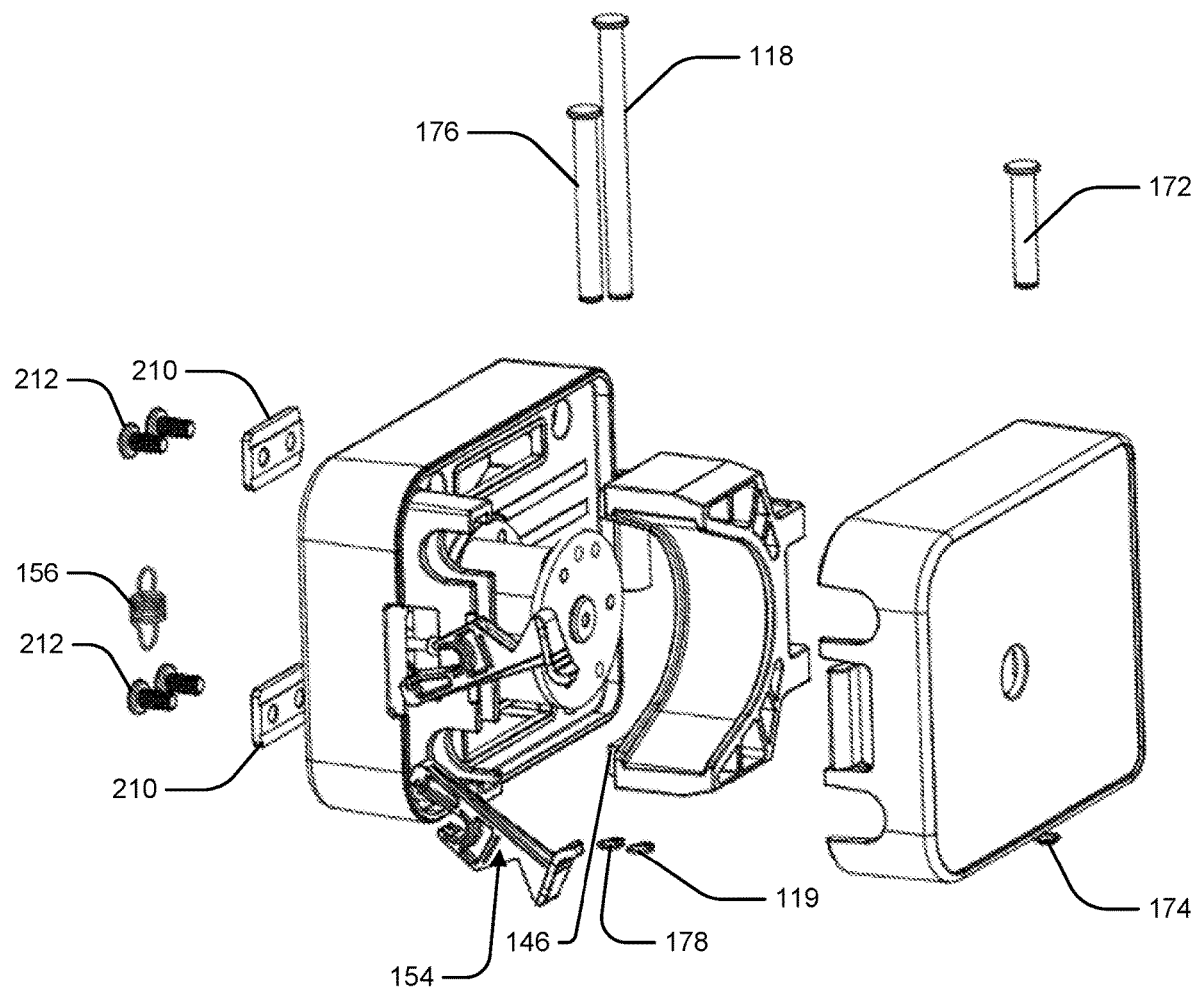
FIG. 2 is an exploded view of the exemplary peristaltic pumphead of FIG. 1, according to an aspect of the disclosure.

FIG. 2 is an exploded view of the example peristaltic pump 100 of FIG. 1. As illustrated, a hinge pin 118 may be inserted into the cylindrical members of the hinge 112 to connect the lid 120 to the base 110 and form the hinge 112. The hinge pin 118 may be held in place by a retainer ring 178, although other types of retainers may be used. Similarly, a hinge pin 172 may be inserted through the arms of the linkage assembly 170 and through the mounting bracket 122 and retained by a retainer ring 174 or other retaining feature to form the hinge 124. Likewise, a hinge pin 176 may be inserted through the occlusion bracket 144 and the cam of the occlusion linkage and retained by a retainer ring 178 or other retaining feature to form the hinge 146.

With respect to the occlusion bed 140, legs 148 may be inserted through the slots 116. Slide blocks 210 may be attached to the legs 148 using screws 212 or other fasteners. The slide blocks 210 may be wider than the slots 116 and ride along the bottom edges of the slots 116 to retain the legs 148, while allowing the legs 148 to slide within the slots 116. The slide blocks 210 may include beveled edges to facilitate positioning and sliding within the slots 116.

With respect to the retainers 154, a spring 156 may be connected to the bottom ends of the retainers 154 to bias the tube engaging notches outward so as to retain received tubing 136.

Figure 3A:
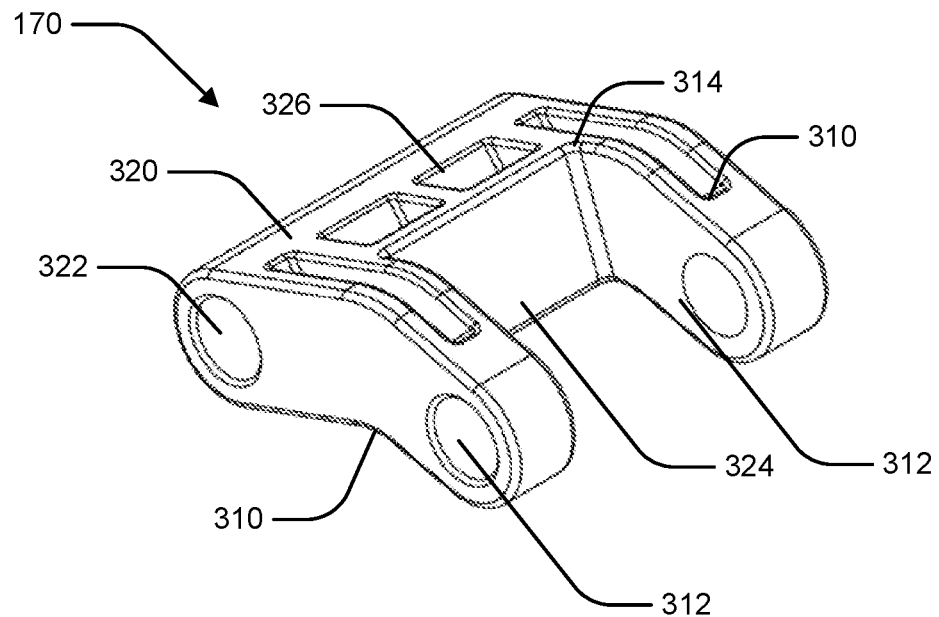
FIG. 3A is a perspective view of an example linkage assembly, according to an aspect of the disclosure.
Figure 3B:
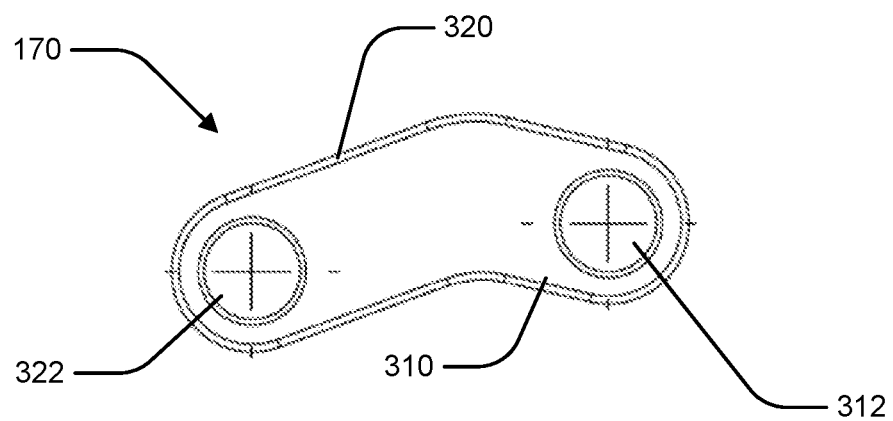
FIG. 3B is a side view of the linkage assembly in FIG. 3A.

FIG. 3A is a plan view of an example linkage assembly 170, according to an aspect of the disclosure. FIG. 3B is a side view of the example linkage assembly 170. The linkage assembly 170 may include at least two curved arms 310 connected by the cam 320. Each arm 310 may include an opening 312 for receiving the hinge pin 172. Each arm 310 may further include an opening 314, which may reduce the mass of the linkage assembly 170. For example, the opening 314 may extend vertically through the arm 310 without affecting the external shape of the linkage assembly 170.

The cam 320 may include a cylindrical opening 322 through the width of the cam 320 for receiving the hinge pin 176. The cam 320 may include a cam surface 324 that abuts the mounting bracket 122 when the lid 120 is in a closed position. The cam 320 may also include one or more openings 326, which extend vertically through the cam 320 and reduce the mass of the linkage assembly 170.

As best seen in FIG. 3B, the arms 310 may be curved. The curvature of the arms 310 may allow the arms to rotate with respect to the mounting bracket 122 to disengage the cam surface 324 from the abutting relationship with the mounting bracket 122. Additionally, the curvature of the arms 310 may provide a desirable movement path and force profile for the occlusion bed 140.

Figure 4:
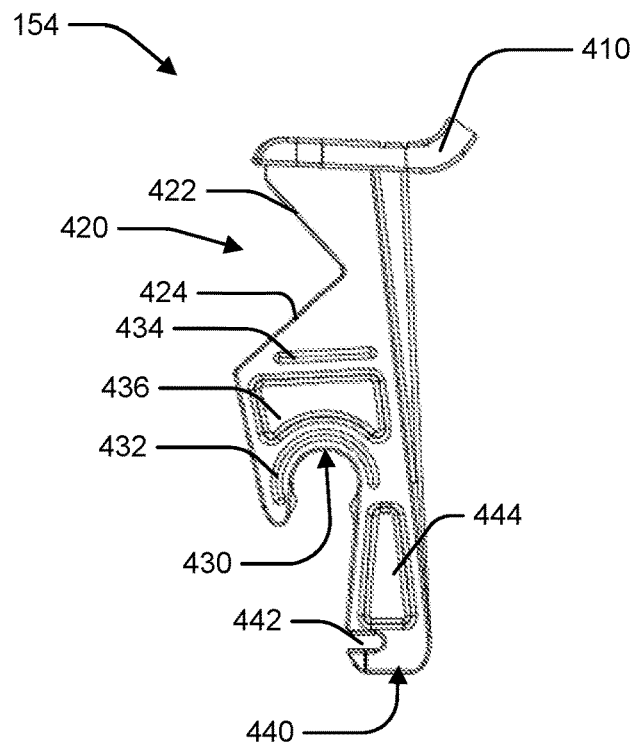
FIG. 4 is a front view of an example retainer, according to an aspect of the disclosure.

FIG. 4 illustrates a front view of an example retainer 154. The retainer 154 may include a grip 410 that may be contacted, for example, by an operator's finger. The grip 410 may include ridges or other features to increase friction. The grip 410 may also include a tab that allows the grip 410 to be pinched. The retainer 154 may further include a notch 420. The notch 420 may have one or more contact surfaces, including a top surface 422 that is substantially perpendicular to a bottom surface 424, such that the notch 420 thereby has a V-shaped cross-section. When the retainer 154 is in a closed position, the top surface 422 and the bottom surface 424 may contact tubing 136 received in the V-shaped cross-section so as to prevent longitudinal movement of the tubing 136. The shape of the notch may help prevent constriction of the tubing 136 at the retainer 154, which may otherwise limit throughput. The retainer 154 may further include a pivot surface 430. The pivot surface 430 may comprise a semi-annular surface that may partially encircles a shaft within the retainer housing 152 when the retainer 154 is engaged therewith. The pivot surface 430 may include tabs or bumps that assist with abuttably retaining the pivot surface 430 on the shaft. The pivot surface 430 may further include an arc shaped ridge 432 extending along an edge of the pivot surface 430. The arc shaped ridge 432 may reinforce the pivot surface 430 and also serve as a spacer to correctly locate the retainer 154 within the retainer housing 152 to allow for pivoting. Similarly, one or more additional ridges 434 may be located on the retainer 154 to provide structural strength or spacing where needed. Openings 436 and 444 may be included within the retainer 154 where structural strength may be exchanged for mass reduction. The retainer 154 may further include a bottom end 440 located opposite the grip 410. The bottom end 440 may include a notch 442 that retains a spring 156 or another biasing element. It should be appreciated that the retainer 154 may be symmetric, such that a single part may be interchangeably used as either a left or right retainer 154 within the retainer housing 152.

Figure 5:
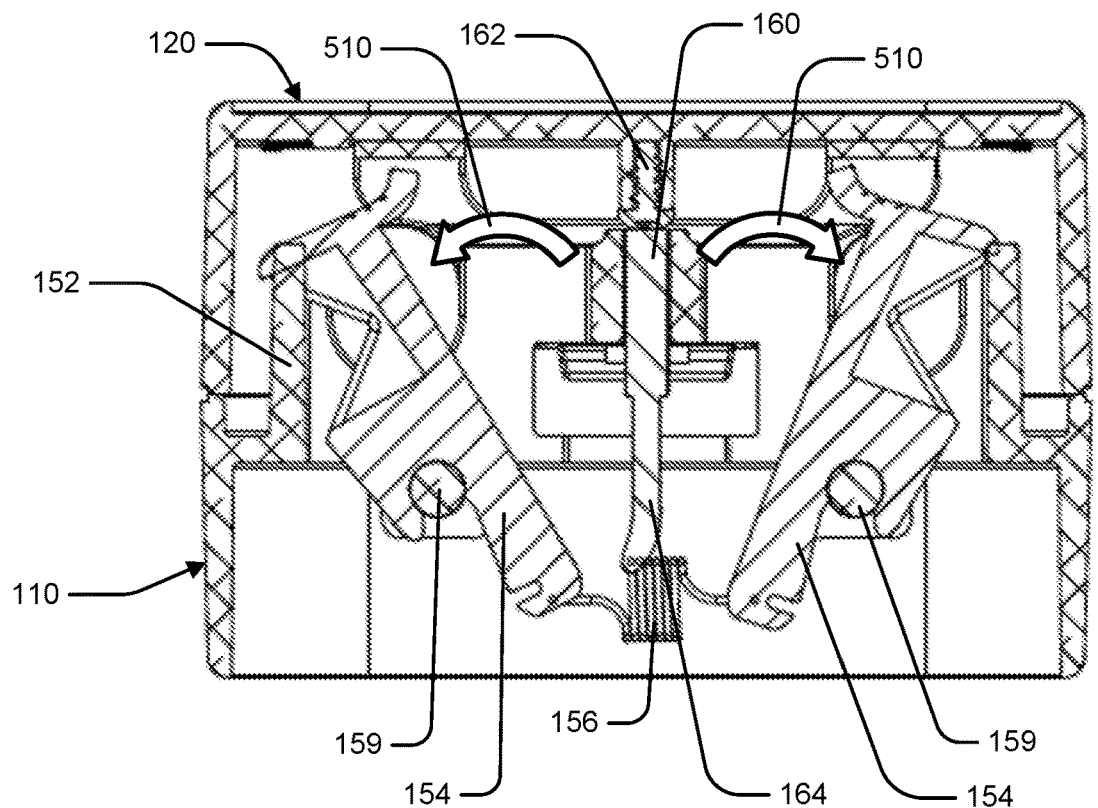
FIG. 5 is a cross-sectional view of the example peristaltic pump of FIG. 1 through a retainer housing.

FIG. 5 illustrates a vertical cross-sectional view of the pump 100 along a section extending through the retainer housing 152. The retainers 154 may be pivotably mounted on the shafts 159. The spring 156 may connect the retainers 154 at the notches 442 and may bias the top surface 422 and bottom surface 424 outward. The lid closed sensor 160 may be centrally located within the retainer housing 152. The lid 120 may include a sensor target 162, which may comprise, for example, a screw or other metallic object that may be detected by the lid closed sensor 160. A wire 164 may carry a signal from the lid closed sensor 160 indicating whether the lid 120 is closed.

Figure 6A:
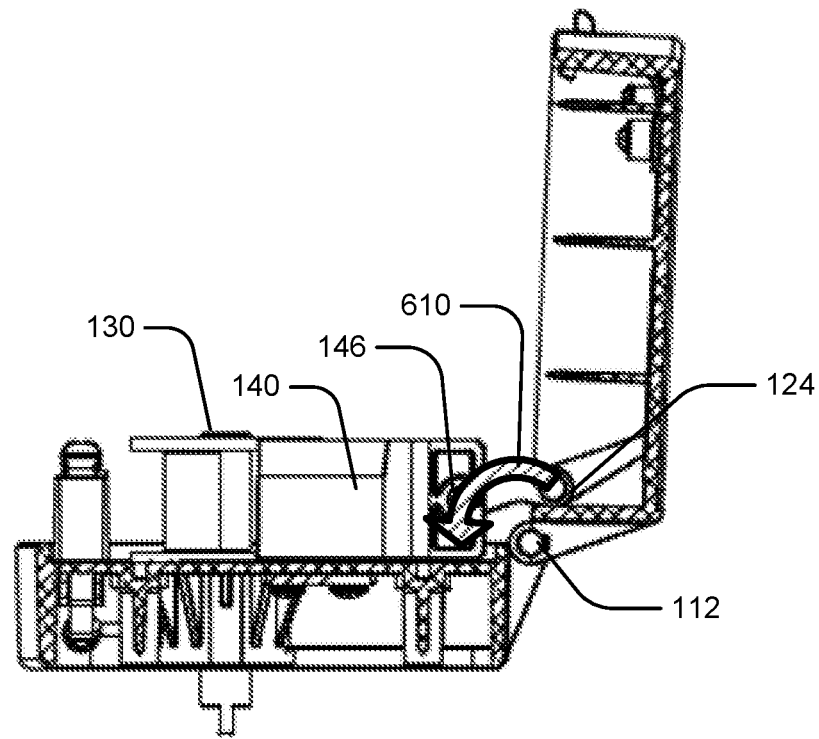
FIG. 6A is a side view of an exemplary peristaltic pumphead in an open position.
Figure 6B:
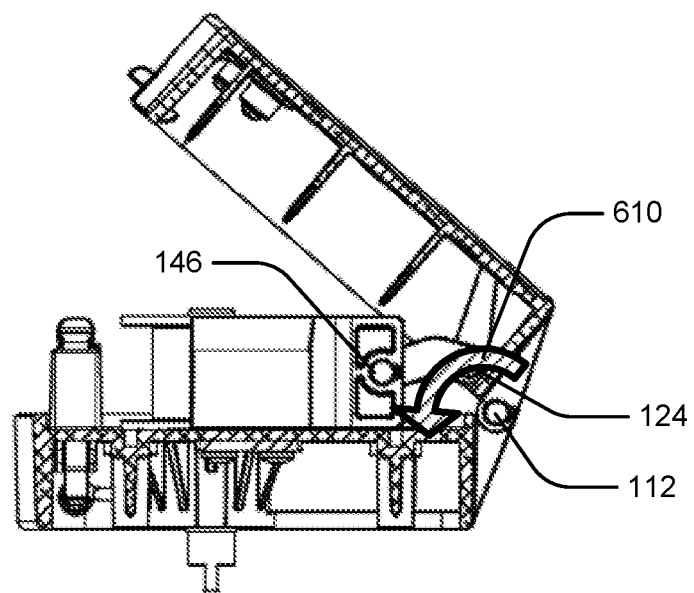
FIG. 6B is a side view of the exemplary peristaltic pumphead in a partially closed position.
Figure 6C:
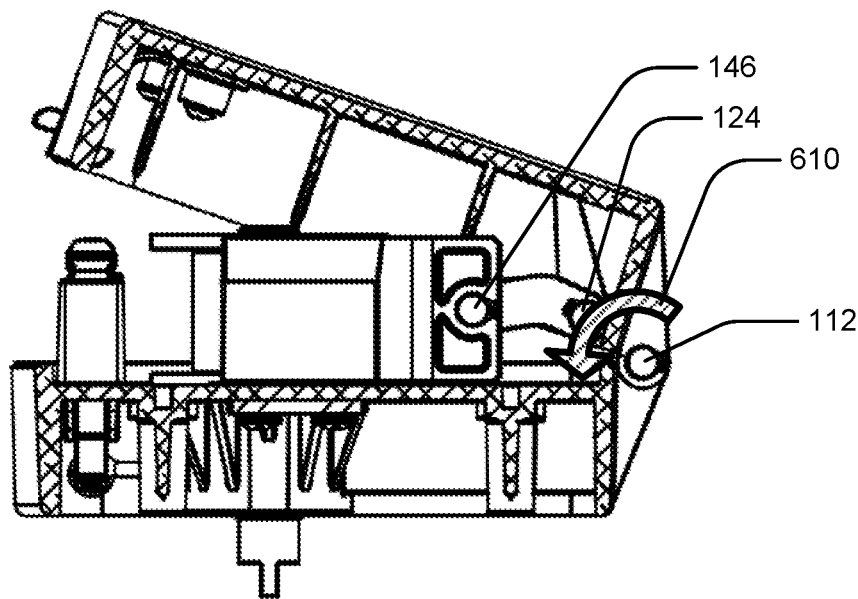
FIG. 6C is a side view of the exemplary peristaltic pumphead in a mostly closed position.
Figure 6D:
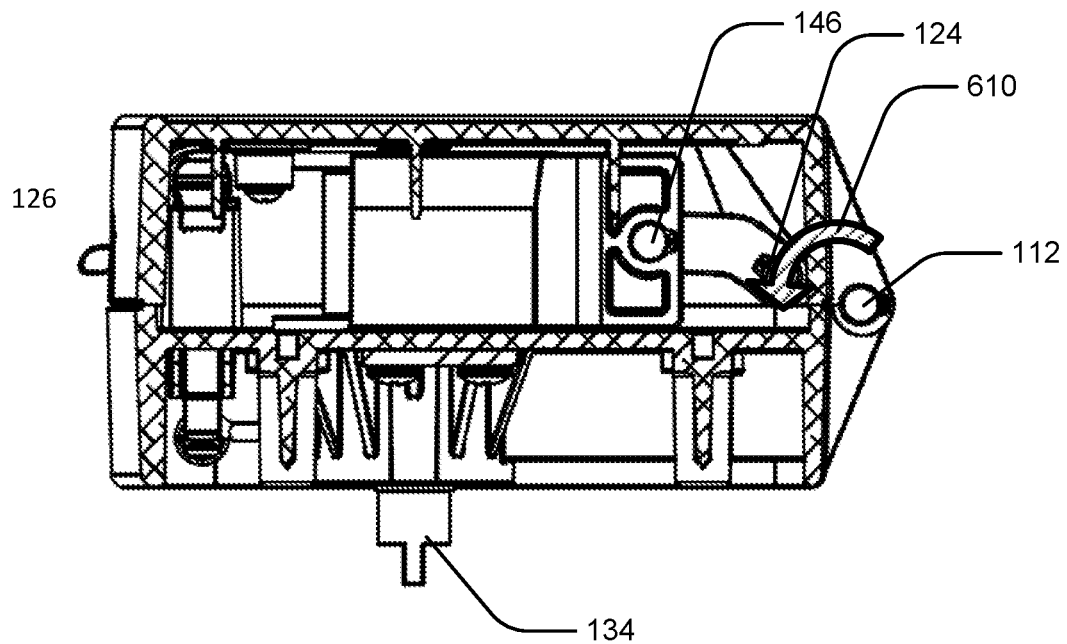
FIG. 6D is a side view of the exemplary peristaltic pumphead in a fully closed position.

FIGS. 6A-6D illustrate side views of the peristaltic pump 100 in positions showing the lid moving from open an position in FIG. 6A to a closed position in FIG. 6D. In FIG. 6A, the occlusion bed 140 may be located in a position closest to the hinge 112 and farthest from the rotor 130. The linkage assembly 170 may be oriented substantially horizontally as shown in the view of FIG. 6A, with the hinge 146 elevated slightly above the hinge 124, as shown. In this position, tubing 136 may be inserted between the rotor 130 and the occlusion bed 140.

In FIG. 6B, the lid 120 has rotated in this view approximately 45 degrees from the position in FIG. 6A. The hinge 124 has described a top portion of an arc 610 about the hinge 112. Accordingly, the hinge 124 may remain elevated in a substantially horizontal orientation slightly above the hinge 146, as shown. The linkage assembly 170 in this position has applied horizontal force to the occlusion bed 140. The occlusion bed 140 has slid horizontally toward the rotor 130.

In FIG. 6C, the lid 120 has rotated approximately 70 degrees from the position in FIG. 6A. The hinge 124 may have started moving downward, as shown in FIG. 6C, relative to the hinge 146 along the arc 610 about the hinge 112, such that the hinge 124 is now located in a position below the hinge 146, in this view. The occlusion bed 140 has moved further toward the rotor 130, but to a lesser degree than when the lid started closing (see, e.g., FIGS. 6A and 6B). Accordingly, the occlusion bed 140 has greater mechanical advantage for compressing the tubing 136 as the occlusion bed 140 approaches the rotor 130.

In FIG. 6D, the lid is shown in a closed position after rotating approximately 95 degrees along the arc 610 from the open position in FIG. 6A. In the last segment, the movement of the hinge 124 may be mostly in a downward direction as shown in FIG. 6D along the arc about the hinge 112. The downward movement brings the cam surface 324 into an abutting relationship with the mounting bracket 122 to form a cooperative connection. The cooperative connection may prevent or inhibit the occlusion bed 140 and linkage assembly 170 from moving toward the hinge 112 when the lid 120 is in a closed position. Additionally, as seen in FIG. 6D, the latch 126 may have moved past the ledge 158 to retain the lid 120 in the closed position, as shown.

When the lid 120 moves in the opposite direction from the closed position in FIG. 6D, toward the open position as shown in FIG. 6A, the hinge 124 of the mounting bracket 122 also describes an arc about the hinge 112. In a first portion of the arc, the direction of movement is primarily in an upward direction away from the base 110. Movement of the curved arms 310 upward while the cam 320 remains relatively stationary allows the mounting bracket 122 to separate from the cam surface 324 before horizontal force is applied to the cam surface 324. As the hinge 124 moves farther along the arc, a horizontal component of the movement as shown in the views of FIGS. 6A-6D increases, such that the hinge 124 moves horizontally in these views away from the rotor 130. The linkage assembly 170 pulls the occlusion bed 140 horizontally in these views away from the rotor 130 to allow removal and/or insertion of tubing 136 between the rotor 130 and the occlusion bed 140.

In an aspect, the components of the peristaltic pump 100 may be fabricated from a high strength plastic using a molding process. Example high strength plastics include glass filled nylon. High strength plastics may be resistant to many different chemicals and may be suitable for use in various environments where peristaltic pumps are used to pump liquids. Additionally, high strength plastics may provide limited flexibility that helps distribute forces, while also providing resistance to wear from cyclic loading of a peristaltic pump.

This written description uses examples to disclose aspects of the invention, including the preferred embodiments, and also to enable any person skilled in the art to practice the aspects thereof, including making and using any devices or systems and performing any incorporated methods. The patentable scope of these aspects is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims. Aspects from the various embodiments described, as well as other known equivalents for each such aspect, can be mixed and matched by one of ordinary skill in the art to construct additional embodiments and techniques in accordance with principles of this application.

The invention claimed is:

1. A peristaltic pump, comprising:
a rotor rotatably mounted on a base of the peristaltic pump;
an occlusion bed mounted on the base of the peristaltic pump and moveable toward and away from the rotor;
a lid hingedly mounted to the base of the peristaltic pump along a first hinge axis, the lid including a mounting bracket extending perpendicularly relative to the first hinge axis; and
a linkage assembly comprising:
a pair of curved arms hingedly mounted to the mounting bracket at a first end of each of the pair of curved arms about a second hinge axis parallel to the first hinge axis; and
a cam connecting each of the pair of curved arms to the other and having a cam surface facing the mounting bracket, the cam being hingedly mounted to the occlusion bed at a second end of each of the pair of curved arms, the second end of each of the curved arms being opposite to the first end;
wherein, when the lid is in a closed position, the mounting bracket extends between the pair of curved arms to abut the cam surface and form a cooperative connection between the lid and the occlusion bed via the linkage assembly.

2. The peristaltic pump of claim 1, further comprising:
a pair of pivoting tubing retainers engaged within a retainer housing opposite the first hinge axis, each tubing retainer including:
a cross-sectionally V-shaped contact portion that engages a tube between an opening in the contact portion and a wall within the retainer housing so as to restrict movement of the tube, wherein each of the pair of pivoting tubing retainers is biased to pivot the contact portion toward the respective wall;
a curved portion that at least partially encircles a shaft in the pumphead housing about which the pivot occurs;
an extending end radially distal to the V-shaped contact portion that includes a gripping surface that allows manual pivoting of the tubing retainer in a direction opposite the biasing so as to reach an open position; and
a biased end opposite the extending end that engages a biasing element.

3. The peristaltic pump of claim 1, further comprising a lid sensor configured to detect whether the lid is in the closed position and enable rotation of the rotor when the lid is in the closed position.

4. The peristaltic pump of claim 1, wherein the linkage assembly is formed of a plastic.

5. The peristaltic pump of claim 1, wherein the linkage assembly is formed of glass filled nylon.

6. The peristaltic pump of claim 1, wherein the linkage assembly is aligned with an axis of rotation of the rotor.

7. The peristaltic pump of claim 1, wherein the cam extends across at least half of a width of the occlusion bed.

8. The peristaltic pump of claim 1, wherein the cam is hingedly mounted to the center of the occlusion bed between bosses protruding from the occlusion bed.

9. The peristaltic pump of, claim 1, wherein the mounting bracket comprises a boss connected to a top surface and a rear wall of the lid.

10. The peristaltic pump of claim 1, wherein the cam is mounted to the occlusion bed via a hinge.

11. The peristaltic pump of claim 1, wherein the hinge includes a through hole in the cam that retains a hinge pin that is also retained within the occlusion bed.

12. The peristaltic pump of claim 1, wherein each of the pair of curved arms has a concave aspect facing toward the base.

13. A method of assembling a peristaltic pump, comprising:

mounting a rotor on a molded base of the peristaltic pump, the base including a rotor receiving opening, a pair of elongated slots, and at least one cylindrical hinge portion;

slidably mounting an occlusion bed on the base though the slots;

inserting a first pivot pin along a first hinge axis through the at least one cylindrical hinge portion and corresponding cylindrical hinge portion of a lid, the lid including a mounting, bracket extending perpendicularly relative to the first hinge axis;

inserting a second pivot pin along a second hinge axis parallel to the first hinge, axis through the mounting bracket and through a first end of each of a pair of curved arms of a linkage assembly including a cam connecting each of the pair of curved arms to the other at a second end of each of the pair of curved arms opposite to the first end and having a cam surface facing the mounting bracket; and inserting a third pivot pin along a third hinge axis parallel to the first hinge axis through the cam and through a bracket of the occlusion bed, wherein, when the lid is in a closed position, the mounting bracket extends between the pair of curved arms to abut the cam surface and form a cooperative connection between the lid and the occlusion bed via the linkage assembly.

* * * * *